United States Patent [19]
Lysaght et al.

[11] Patent Number: 5,232,437
[45] Date of Patent: Aug. 3, 1993

[54] MOBILE, SELF-CONTAINED BLOOD COLLECTION SYSTEM AND METHOD

[75] Inventors: Michael J. Lysaght, Barrington; Daniel R. Boggs; Philip L. Ritger, both of Vernon Hills, all of Ill.; Robert R. Stromberg; Leonard I. Friedman, both of Silver Spring, Md.

[73] Assignee: Baxter International Inc., Deerfield, Ill.

[21] Appl. No.: 496,739

[22] Filed: Mar. 21, 1990

Related U.S. Application Data

[63] Continuation of Ser. No. 296,850, Jan. 12, 1989, Pat. No. 4,911,903, which is a continuation of Ser. No. 919,346, Oct. 15, 1986, abandoned.

[51] Int. Cl.$^5$ ............................................. A21M 25/00
[52] U.S. Cl. ........................................ 604/6; 604/4; 604/5; 210/90
[58] Field of Search ............................ 604/4–6; 210/90

[56] References Cited

U.S. PATENT DOCUMENTS

| | | |
|---|---|---|
| Re. 32,089 | 3/1986 | Blatt et al. |
| 2,502,081 | 1/1950 | Flynn et al. |
| 3,151,616 | 1/1964 | Selfon |
| 3,198,385 | 1/1965 | Maxwell |
| 3,543,966 | 2/1970 | Ryan |
| 3,640,277 | 8/1972 | Adelberg |
| 3,647,117 | 3/1972 | Hargest |
| 3,655,123 | 4/1972 | Judson et al. ............ 604/6 X |
| 3,670,926 | 6/1972 | Hill |
| 3,895,741 | 7/1975 | Nugent |
| 3,902,490 | 8/1975 | Jacobsen et al. |
| 4,027,784 | 6/1977 | Mattson |
| 4,044,764 | 6/1977 | Szabo et al. |
| 4,191,182 | 3/1980 | Popovich et al. ......... 604/6 |
| 4,212,742 | 7/1980 | Solomon et al. |
| 4,237,881 | 7/1980 | Beigler et al. |
| 4,284,502 | 8/1981 | Kramer |
| 4,381,775 | 5/1983 | Nose et al. |
| 4,447,191 | 5/1984 | Bilstad et al. |
| 4,458,539 | 5/1984 | Bilstad et al. |
| 4,479,760 | 10/1984 | Bilstad et al. |
| 4,479,761 | 10/1984 | Bilstad et al. |
| 4,479,762 | 10/1984 | Bilstad et al. |
| 4,481,827 | 11/1984 | Bilstad et al. |
| 4,493,693 | 1/1985 | Bilstad et al. |
| 4,498,983 | 7/1985 | Bilstad et al. |
| 4,526,515 | 7/1985 | DeVries |
| 4,551,136 | 11/1985 | Mandl |
| 4,551,139 | 11/1985 | Plaas et al. |
| 4,557,728 | 12/1985 | Sealfon et al. |
| 4,573,962 | 2/1986 | Troutner |
| 4,588,407 | 5/1986 | Isono et al. |
| 4,605,503 | 8/1986 | Bilstad et al. |
| 4,614,513 | 4/1986 | Bensinger |
| 4,630,078 | 12/1987 | Sprague |
| 4,639,243 | 1/1987 | Schmidt et al. |
| 4,655,742 | 4/1987 | Vantard |
| 4,713,171 | 12/1987 | Polaschegg |

FOREIGN PATENT DOCUMENTS 0114698  8/1984  European Pat. Off.
0175618  3/1986  European Pat. Off.

OTHER PUBLICATIONS

Supplemental European Search Report issued in EP 87907371.
European Search Results regarding European Application No. 87907371.6 dated Feb. 22, 1990 with cited references.

Primary Examiner—Robert A. Hafer
Assistant Examiner—Kerry Owens
Attorney, Agent, or Firm—Paul C. Flattery; Bradford R. L. Price; Daniel D. Ryan

[57] ABSTRACT

Methods and systems for collection of blood components, such as plasma, from donors are provided. One method includes the steps of collecting a unit of whole blood from a donor; forcing the collected blood unit through a plasma separator; accumulating the plasma in a container; and returning concentrated cells to the donor. One system includes a disposable blood collection set and a reusable fixture into which the collection set can be mounted. The fixture is operated by a self-contained energy source, requiring no exterior electrical connection or other external source of energy.

46 Claims, 6 Drawing Sheets

MOBILE, SELF-CONTAINED BLOOD COLLECTION SYSTEM AND METHOD

This is a continuation of application Ser. No. 07/296,850, filed Jan. 12, 1989 now U.S. Pat. No. 4,911,703, which in turn is a continuation of application Ser. No. 06/919,346, filed Oct. 15, 1986 now abandoned.

Technical Field

The invention pertains to the field of blood component collection. More particularly, the invention pertains to the collection of blood components, especially plasma, from donors using lighweight equipment capable of easy transport.

Background of the Invention

The development of single needle, disposable blood collection systems has provided a safe, relatively inexpensive and accepted modality for collecting whole blood from donors. The whole blood (which is collected in units of 450 ml) is usually centrifugally separated into various therapeutic components, such as red blood cells, platelets, and plasma, for direct transfusion or further processing into other therapeutic products. Such systems have made possible large-scale collection of whole blood from volunteer donors at sites such as church halls, schools or offices remote from medical facilities. The availability whole blood collection systems suitable for volunteer donors is important, because it provides access to a relatively large pool of healthy individuals from which to draw needed supplies of whole blood components for life-saving or therapeutic purposes.

The conventional whole blood collection systems, familiar to and accepted by volunteer donors, can be used to collect plasma, as just described. However, such systems, by design, yield only approximately 250 to 300 ml of plasma per donor. Furthermore, such systems, by design, also take red blood cells from the donor. The donor must internally replace red blood cells before he or she can donate again. Current governmental regulations in the United States prescribe a waiting period of 56 days, during which time the red blood cell donor cannot give blood. Thus, such conventional whole blood collection systems are limited for the collection of relatively large pools of plasma from which the various therapeutic plasma proteins, such as albumin and AHF (anti-hemophilic factor), are obtained by a process called fractionation.

The collection of only plasma from volunteer donors, as opposed to the collection of whole blood, is not widespread. As a result, much of the plasma now collected for fractionation purposes comes from paid donors, not volunteer donors. It would be desirable to make the collection of plasma a volunteer-based activity to a much greater extent than it is currently.

Various methods are known for the collection of only plasma from a donor (also called plasmapheresis). For example, using a modification of the above-described whole blood collection system, a unit of whole blood is collected and separated by centrifugation into red blood cells and plasma. The plasma is retained, while the red blood cells are immediately returned to the donor. The process is then repeated, collecting additional plasma and returning the red blood cells. The result is the collection of 500 to 600 ml of plasma for fractionation purposes. Because red blood cells are returned to the donor, this process allows more frequent donation, often as frequently as twice per week. However, this process is time-consuming and, in part for this reason, does not appeal to volunteer donors. Furthermore, during the process, while the whole blood is being separated into red blood cells and plasma, the blood collection system (typically a series of integrally attached bags) is physically separated from the donor. Such physical separation requires procedures to minimize the risk of error when several donors are being processed simultaneously that one donor's red blood cells are not inadvertently returned to another donor. In addition, physical separation of the blood from the donor could potentially raise concerns in the collection staff of exposure to infectious agents in the collected blood if fluid drips or leaks occur.

On-line extracorporeal separation systems, in which the blood collection system is not physically separated from the donor during the collection procedure, are also known. These can be either batch or continuous systems. Such systems employ either centrifugal separators or membrane filters.

A centrifuge-based system is disclosed in Judson et al. U.S. Pat. No. 3,655,123 entitled "Continuous Flow Blood Separator". The system of the Judson et al. patent was two needles, an outflow needle and an inflow needle. Whole blood is drawn from a donor via the outflow needle. The whole blood fills a buffer bag. Blood from the buffer bag drains, under the force of gravity into a centrifuge. The system of the Judson et al. patent uses the centrifuge to separate blood components. The plasma can be collected in a container. The red blood cells can be returned to the donor via the inflow needle.

A membrane-based system is disclosed in Popovich et al., U.S. Pat. No. 4,191,182.

The systems of the Judson et al. and Popovich et al. patents require an external source of electrical energy. Further, the systems rely upon a variety of heavy and somewhat delicate electro-mechanical components, including pumps and the centrifuge that prevent it from being readily portable. Such systems that include pumps are often constant volume systems, in which a relatively constant volume of fluid is pumped through the system per unit of time. Constant volume systems suffer from the disadvantage that undesirable, over pressure conditions can occur if one of the fluid flow lines is crimped or partly closed. The systems also require that the donor be subjected either to two needle punctures (one in each arm) or a large bore double lumen needle, neither of which are favored by volunteer donors. Finally, since these relatively complex systems are intended to be coupled to one donor at a time, multiple simultaneous donations would be prohibitively expensive.

The known extracorporeal separation systems are therefore expensive, complex, not "donor friendly", and generally unsuited for portable operation.

One system of membrane collection suitable for portable operation has been described in a published European Patent Application, Publication No. 0114698 published Aug. 1, 1984; entitled "Process and Apparatus for Obtaining Blood Plasma." In this system, a unit of blood is withdrawn from a donor into a set containing a membrane filter, tubing and a sterile blood container (such as a conventional blood bag). The whole blood is first passed through the filter. The plasma flows through the membrane filter and is collected in a separate plasma container. The remainder of the blood unit, which had passed from the inlet to the outlet of the filter, is accumulated in the sterile container. It can then be immediately returned to the donor.

In this approach, the pressure available for driving the filtration process and for propelling the blood from the inlet to the outlet of the filter is relatively small. This pressure includes the donor's venous pressure (which, with an inflated pressure cuff on the donor's arm, is on the order of 40 mm Hg) and available hydrostatic head (approximately 50 mm Hg) for a total pressure on the order of 90 mm Hg. These pressures may vary significantly from donor to donor. This can result in a relatively slow and variable plasma collection time. It also requires relatively large filters to function at the available low driving pressures. It can also be difficult to achieve precise anticoagulant flow proportional to blood flow with inexpensive and simple-to-use hardware.

Another membrane-based system is disclosed in a group of three U.S. Pat. No. 4,479,760 entitled "Actuator Apparatus for a Prepackaged Fluid Processing Module Having Pump and Valve Elements Operable in Response to Applied Pressures"; U.S. Pat. No. 4,479,761 entitled "Actuator Apparatus for a Prepackaged Fluid Processing Module Having Pump and Valve Elements Operable in Response to Externally Applied Pressures"; and U.S. Pat. No. 4,479,762 entitled "Prepackaged Fluid Processing Module Having Pump and Valve Elements Operable in Response to Applied Pressures," all issued to Bilstad et al. The system of the Bilstad et al. patents utilizes a disposable module containing a hollow membrane filter, a plasma container and other elements. A fixture is provided to receive the module during the donation cycle. Constant volume pumps in the fixture are provided to draw whole blood from the donor into the inlet side of the filter and to return the concentrated red cells to the donor from the outlet side of the filter. A single needle is used from both drawing the whole blood from the donor and returning concentrated red blood cells to the donor.

The system of the Bilstad et al. patents requires an exterior source of electrical energy. In addition, the fixtures can be relatively expensive and complex.

SUMMARY OF THE INVENTION

The invention provides methods and systems for the separation and collection of blood components which offer both efficiency and simplicity of operation.

In one aspect of the invention, a blood component collection method and associated system are provided in which a desired volume of whole blood is accumulated in a container and a force is then applied to express the accumulated whole blood from the container and into a separator. In the separator, the whole blood is separated into component parts.

In one preferred embodiment, the whole blood is collected in a variable volume container, and the force is applied upon the container to reduce its volume and thereby express the accumulated whole blood into the separator, preferably at a substantially constant pressure.

The above described method and associated system are particularly well suited for the collection of plasma using a membrane filtration device as the separator. The use of substantially constant pressure lends itself to optimization of the filtration technique.

In another aspect of the invention, a blood component separation system is provided employing a fixture on which a variable volume container is retained in flow communication with a separation device. The fixture includes a means for applying a force upon the container to express its contents into the separation device. The energy source to activate the force application means is carried by the fixture, so that reliance upon an external energy source, such as by connection to an external electrical source, is eliminated.

In one embodiment, the energy source comprises means for selectively storing a quantity of energy on the fixture, along with means for selectively introducing energy into the energy storage means.

In another embodiment, the energy source includes means for releasably receiving a module containing a releasable charge of energy and for releasing this energy charge upon demand to selectively operate the force application means.

This aspect of the invention provides a blood component separation apparatus which can be readily transported to temporary locations, such as churches and schools, to collect blood components from volunteer donors. The apparatus is self-contained and does not require an external electrical connection or an external source of energy.

Other features and advantages of the present invention will become readily apparent from the following detailed description, the accompanying drawings, and the appended claims.

DETAILED DESCRIPTION OF THE PREFERRED EMBODIMENT

The present invention has many diverse embodiments. Several alternate embodiments are shown and described. However, it should be understood that the present disclosure is to be considered as an exemplification of the invention, and is not intended to limit the invention to the specific embodiments illustrated.

Figure 1:
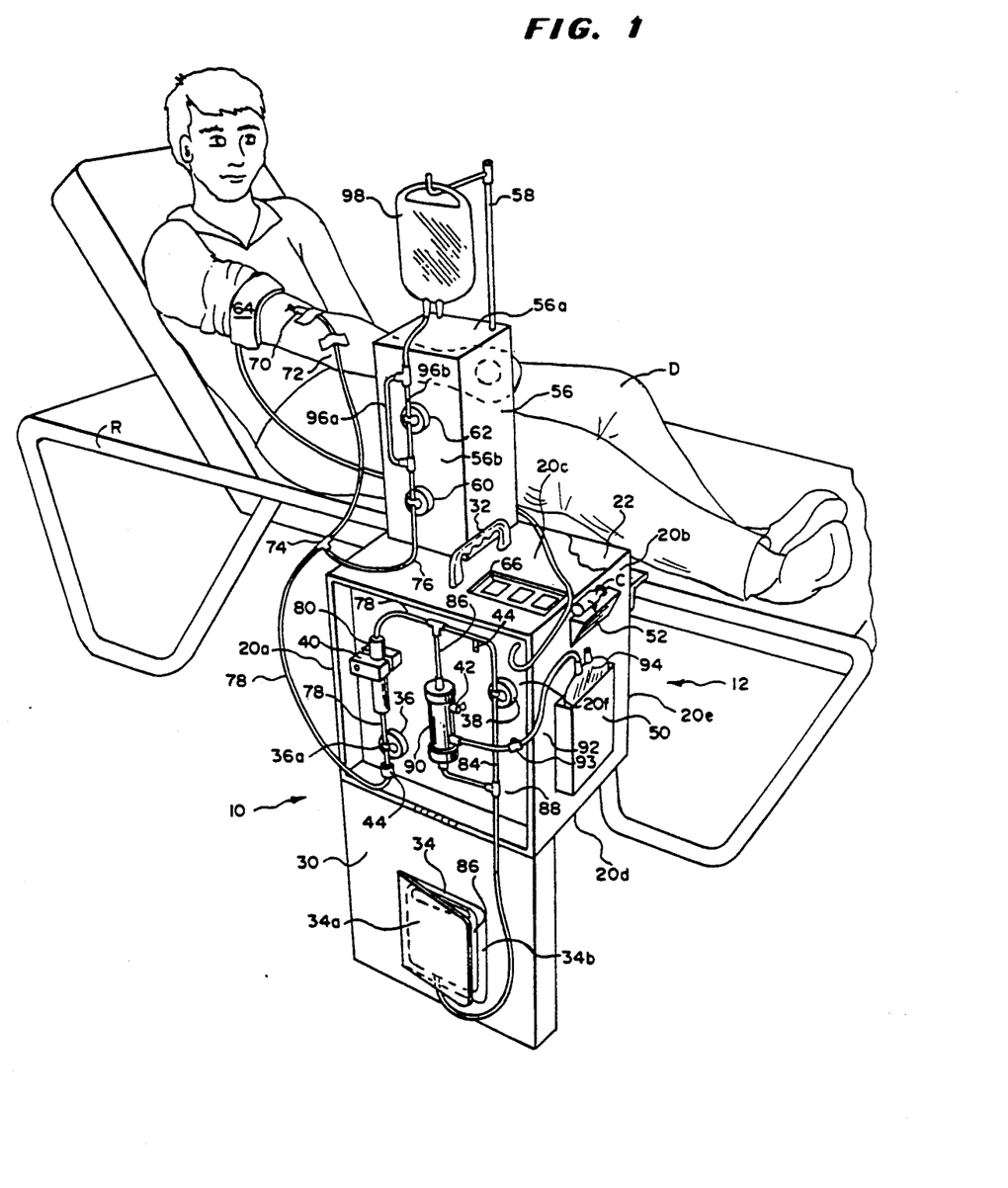
FIG. 1 is a perspective view of a plasmapheresis system, configured for use, in accordance with the present invention.
Figures 2, 3:
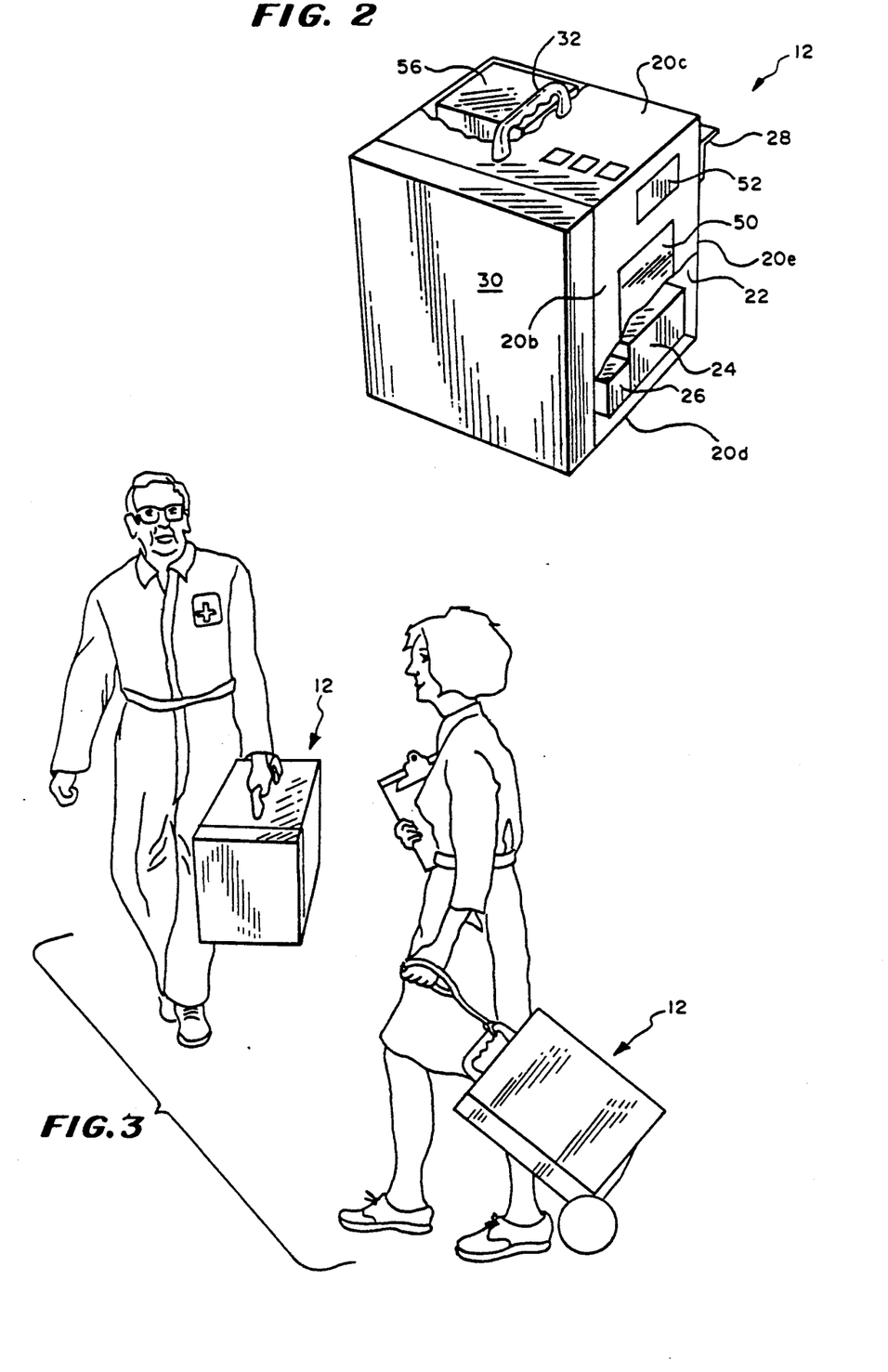
FIG. 2 is a perspective view, partly broken away of a fixture, configured for transportation, in accordance with the present invention.
FIG. 3 is a pictorial view illustrating portability of the fixture in FIG. 2.

A self-contained, portable system 10 usable for the collection of blood components from donors is illustrated in FIGS. 1 to 3. In the particular embodiment, the system 10 is intended to collect plasma from volunteer donors. In this embodiment, the system 10 includes a portable, self-contained and reusable fixture 12. The system 10 also includes a single-use, disposable, integrally-formed tubing set 14. The set 14 is mounted in the fixture 12 during the collection process.

The fixture 12 includes a housing 20 which can be formed of a metal or plastic. The housing 20 has sides 20a, 20b; a top and bottom 20c, 20d and rear surface 20e. Housing 20 defines or forms a closed interior region 22 in which is located a control unit 24 (see FIG. 2).

Affixed to the rear surface 20e is a pair of clamps 28. The clamps 28 are intended to engage a rail R of a blood donation cot or bed, as shown in FIG. 1. Such cots are currently regularly used in connection with the collection of whole blood from volunteer donors.

The clamps 28 support the fixture 12 at an appropriate working height without any need for supporting legs or tables. The clamps 28 fold flat against the rear surface 20e for storage and transportation.

The housing 20 has a hinged front cover 30. During transportation, the cover 30 is closed and latched. The overall size of the fixture 12 when closed for the transportation and storage is on the order of 12" wide by 12" deep by 14" high. A handle 32 is attached to the top surface 20c for use during transportation.

The hinged cover 30 holds, below the donor D, a whole blood collection container support or receptable 34 with a hinged cover 34a. Located in the blood container support 34 is a force applying system 34b.

The fixture 12 also includes an energy source 51 for the force applying system 34b, as well as for the control system 24. The source 51 is self-contained in the housing 20, so that operation of the fixture 12 is independent of any external source of energy.

A recessed front panel 20f on the housing 20 supports clamps 36 and 38, a bubble sensor 40, a plasma separator support clamp 42 and tubing supports 44. The clamps 36, 38 are of a type conventionally used to close off flexible tubing members, and can take the form of pneumatically operated clamps. In this arrangement, in an unenergized condition, a spring biased clamping bar, such as the bar 36a, pinches the tubing in the clamp closed. When energized, by fluidic pressure, the clamping bar moves away from the tubing member permitting fluid to flow. The bubble sensor 40 is an ultrasonic sensor of a type conventionally used with blood donation and return systems to sense a gas-liquid interface. The sensor 40 is powered by a battery 26 housed within the interior region 22 (see FIG. 2).

Support 42 could be a spring clamp capable of removably supporting a cylindrical plasma separator such as a filter. Tubing supports 44 can correspond to small, L-shaped hangers of a type used to temporarily support flexible tubing.

Slidably affixed to the side 20b is a plasma container support 50. The support 50 can be a three-sided housing with a bottom but no top. Part of the side 20b forms the fourth side or the support 50. When the fixture 12 is being transported, the support 50 is pushed flat against the side 20b, as shown in FIG. 2.

While the energy source 51 can be variously constructed, in the embodiment shown in FIGS. 1 to 5, the source 51 includes a hinged cover and receiver 52. The receiver 52 can be opened to receive a module containing a releasable charge of energy. In the illustrated embodiment, the module takes the form of a $CO_2$ cartridge C inserted in the fixture 12 to provide a modular, self-contained fluidic, charge of energy to actuate the fluidic control system 24, the force applying system 34b, as well as the clamps 36, 38, 60 and 62. Alternately, the module can take the form of a batter, either single use or rechargeable.

A pop-up column 56 extends from the top 20c. The column 56 supports an L-shaped, tubular, anticoagulant support member 58 at a top surface 56a. The L-shaped support member 58 provides a hanger for a container of anticoagulant solution. The pop-up column 56, on a front surface 56b supports two additional tubing clamps 60 and 62. The clamps 60, 62, as is discussed subsequently, are used to regulate the flow of anticoagulant when the system 10 is in use. For storage or transportation, the tubular support member 58 is retractable into the column 56. The column 56 is in turn pushed downward into the region 22. The top surface 56a then is positioned adjacent the top 20c of the fixture 12.

An inflatable cuff 64 is provided, coupled to the control unit and timer 24. A control panel 66 with a plurality of push buttons is positioned on the surface 20c.

FIG. 2 illustrates the fixture 12 with the cover 30 closed and the column 56 retracted for storage and transportation. The fluidic control unit 24 and the battery 26 are also illustrated in FIG. 2 positioned in the interior region 22. The hangers 28 can be closed flat against the surface 20e during transportation.

FIG. 3 illustrates the portability of the fixture 12 when it is being taken to donation sites. The fixture 12 can be easily carried or pulled on a small cart of the type used to transport luggage. When the fixture 12 arrives at the donation site, it is mounted on the side of an available donor bed, as illustrated in FIG. 1 and opened. The tubing set 14 can be mounted in the fixture 12. The modular $CO_2$ cartridge C can be inserted in the receiver 52, and used to energize the fixture 12. No additional exterior source of energy is needed to actuate the fluidic control system 24, the force applying system 34b, and the clamps 36, 38, 60 and 62 of the fixture 12 to carry out the donation process. Provision can be made in the fixture 12 for a storage region in which additional cartridges can be kept prior to use.

As an alternate to the column 56, the housing 20 can be elongated and the clamps 60, 62 can be mounted on the recessed surface 20f, above the tubing member 78. In this embodiment, the clamps 60, 62 would be spaced apart horizontally from one another.

As an alternate to the clamps 28, the fixture 12 can be fitted with a pair of foldable or telescoping rear legs. In this embodiment, the foldable front cover 30, when opened, can function as a front support. The fixture 12 in this embodiment will be self-supporting and will stand on the floor beside the donor bed.

Figure 4:
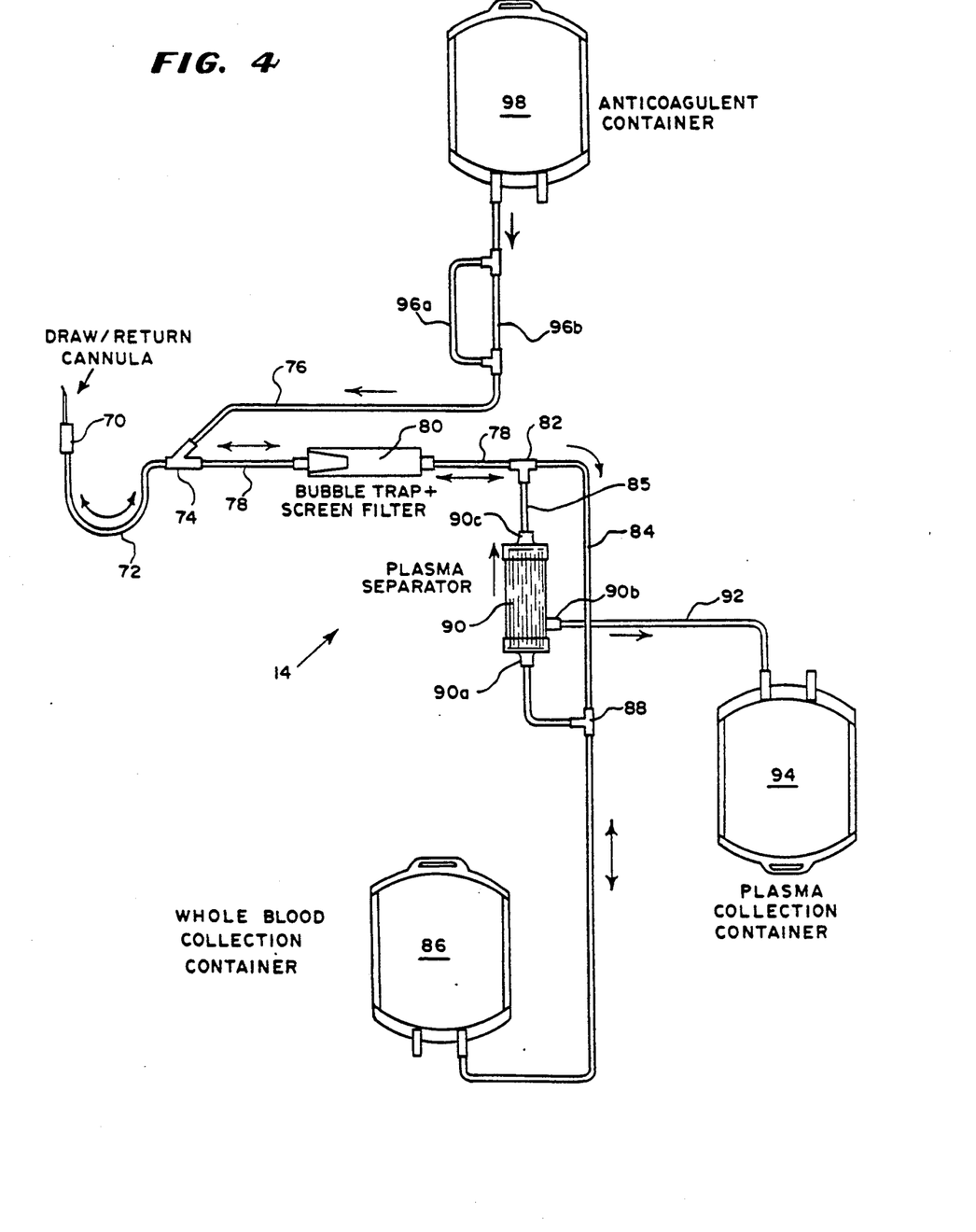
FIG. 4 is a planar view of a blood contacting set in accordance with the present invention.

FIG. 4 illustrates details of the set 14. The set 14 includes a single lumen draw/return cannula or phlebotomy needle 70. The cannula 70 has pointed end that can be inserted into a vein of a donor D, to provide access to the donor's whole blood.

The cannula 70 is coupled to a flexible fluid flow conduit or tubular member 72. The member 72 is coupled to a Y-shaped junction 74. The junction 74 is in turn coupled to an anticoagulant delivering tubular member 76 and a tubular member 78. The member 78 alternately receives whole blood from the cannula 70 and returns concentrated red blood cells to the donor D.

A combined bubble trap and screen filter unit 80 is located in the line 78. The unit 80 is conventional device manufactured by Travenol Laboratories, Inc.

A T-shaped coupling member 82 couples the tubing member 78 to tubing members 84 and 85. Tubing member 84 is in fluid flow communication with a whole blood collection container 86. The container 86 is preferably a variable volume container, meaning that the interior volume of the container expands to accommodate the introduction of fluid and can be contracted to reduce the interior volume so as to expel or displace the fluid contents. The variable volume container 86 can correspond to a flexible, conventional, blood collection bag. It can also correspond to a rigid or semirigid container which includes a collapsible portion to reduce its interior volume.

A T-shaped coupling member 88 is located in the line 84. The member 88 also places the collection bag 86 into fluid flow communication with an inlet 90a of a blood component separator 90, which, in the illustrated embodiment, separates plasma from the other components of whole blood, notably red blood cells, white blood cells, and platelets. The plasma separator 90 can be implemented in a variety of ways. For example, and without limitation, the separator 90 could be implemented as a chromotography column, an electrophoretic apparatus, an immunoabsorbant column or a membrane filter. The filter could incorporate planar membrane sheets, or cylindrical membrane fibers, and can also include a means for rotating the filter to enhance its filtration efficiencies. In a preferred form of the invention, the plasma separator is implemented as an optimized, hollow fiber membrane filter.

Coupled to and in fluid flow communication with a plasma output port 90b, via a flexible tubular member 92 is a plasma collection container 94. The container 94 could be a flexible plastic container similar to the container 86. An outlet 90c of the separator 90 is coupled to the tubular member 85.

The anticoagulant delivery member 76 is coupled via tubular members 96a and 96b to a container 98 of anticoagulant solution. The member 96a has a smaller internal diameter than does the member 96b. By means of these two flow paths, the anticoagulant can be easily and cheaply metered into the blood being collected via the tubing member 78. The arrows on FIG. 4 indicate directions of fluid flow when the set 14 is used with the fixture 12.

The tubing members of the set 14 can be formed of conventional, flexible plastic of a type suitable for contacting blood. The containers can be formed of conventional plastic now used in blood collection sets. Preferably, the set 14 comprises a sterile, integrally connected unit.

Figure 5:
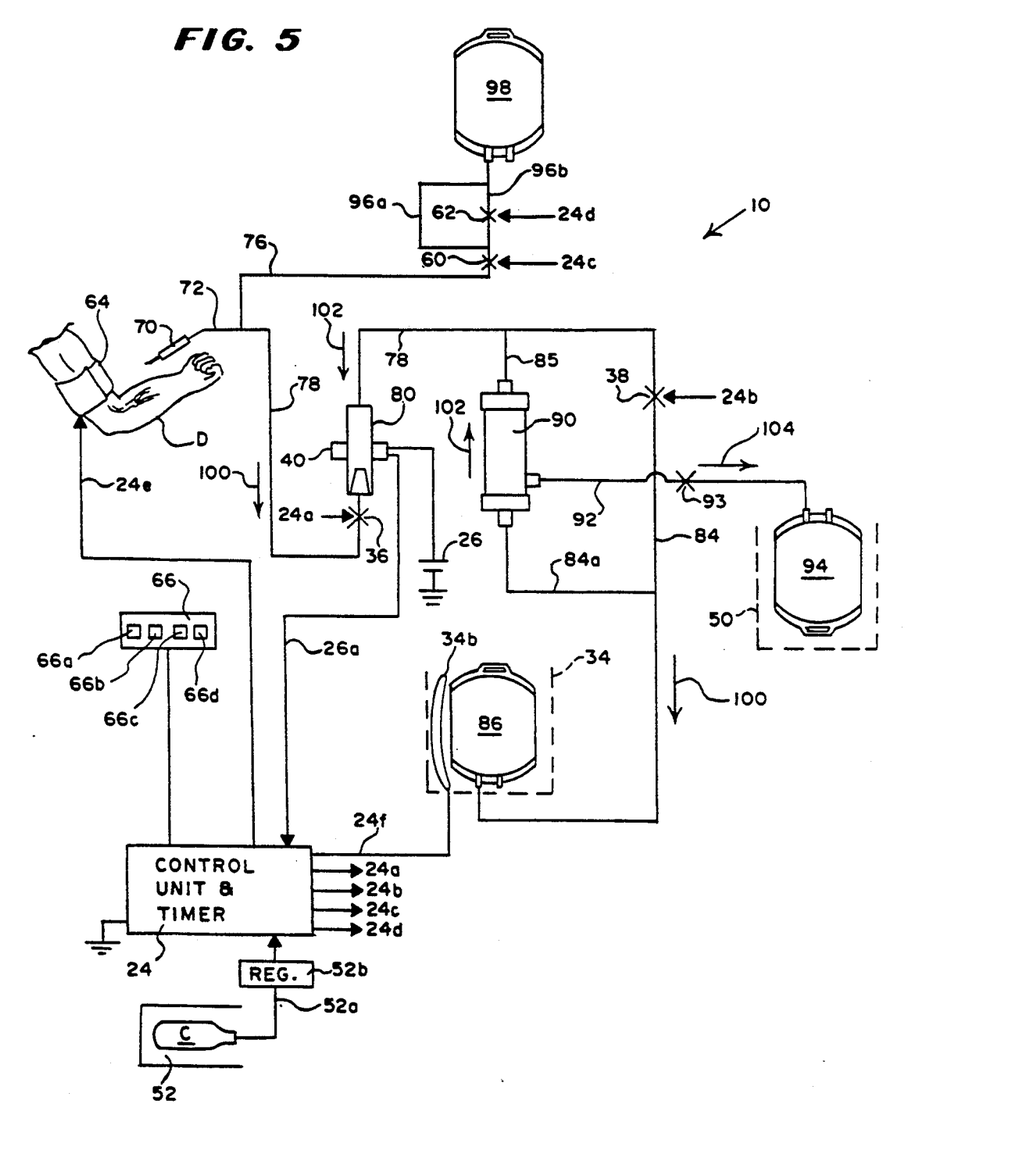
FIG. 5 is a schematic diagram of an apparatus and method for plasmapheresis in accordance with the present invention.

FIG. 5 illustrates the system 10 schematically. The fluidic control unit and timer 24 are coupled to the fluidic source of energy C via a fluid flow input line 52a and a regulator 52b. The control unit and timer 24 are also coupled via a plurality of fluid flow lines 24a, 24b, 24c and 24d the fluid actuatable clamps 36, 38, 60 and 62, respectively. The unit 24 can selectively open each of the clamps 36, 38, 60 and 62 by providing fluidic energy on the respective line 24a, 24b, 24c and 24d. Fluidic line 24e couples the unit 24 to the inflatable cuff 64.

The bladder 34b can be inflated and deflated by the unit 24 via a fluidic control line 24f. The control unit and timer 24 receive electrical signals on the line 26a from the battery powered bubble detector 40. If the electrical signal on the line 26a indicates that a bubble has been detected in the line 78 during a return cycle, as discussed subsequently, the control unit 24 will permit clamp 36 to close thereby blocking any further flow in the line 78 to the donor D. An alarm condition can also be indicated on the panel 66.

The control unit and timer 24 can be implemented of standard fluidic logic components in accordance with the donor and return cycle described herein. The electrical signal on the line 26a can be coupled to a solenoid valve in the unit 24.

FIG. 5 illustrates use of the mobile plasma collection system 10 in accordance with the present invention. The donor D is positioned adjacent to the sterile, sealed collection system 10. The system 10 includes the set 14 with the cannula 70, which could be a conventional, sterile single lumen phlebotomy needle of a type used in connection with blood collection. The needle 70 is coupled via flexible tubing 72, 78 and 84 of a conventional variety to the whole blood collection container or bag 86.

The collection bag 86 could be a flexible 500 ml plastic bag of a type now used for blood collection. The fluid operable clamp or valve 38 can be used to close off tubing member 84 under control of the unit 24. Closing the value 38 isolates the donor D from direct fluid flow communication from the container 86. Arrow 100 indicates the direction of flow of collected blood from the donor D into the collection bag 86. The whole blood drains from the donor D into the container or bag 86, as a result of the donor's internal blood pressure, which can be elevated in the region of the needle 70 by inflating the pressure cuff 64, as well as the force of gravity.

The container 86 is filled from the bottom as illustrated in FIGS. 1 and 5. Average fill time with a normal donor will be in a range of 4-7 minutes. The draw rate with an average donor will be in a range of 70-100 ml/minute.

Anticoagulant solution is metered from the container 98 through the two-part conduit 96a, 96b of known resistance. The anticoagulant solution is metered into the blood simultaneously with the whole blood being collected from the donor D.

The two tubes 96a and 96b each have a selected diameter and length. The tube 96a has a smaller diameter than does the tube 96b. By having both tubes 96a and 96b open simultaneously for a selected period of time and then closing one tube off while the other remains open, the rate of flow and quantity of anticoagulant mixed with the blood flowing through the member 72 can be regulated. Valve 62 can be used to close off the larger diameter conduit 96b under control of the unit 24. The dual tube system with members 96a, 96b makes it possible to keep the level of anticoagulant in the blood in the lumens of the tubing members, such as the member 78, and in the collection bag 86 between predetermined upper and lower limits even though donor blood rate is variable.

When the donor D has provided a unit of whole blood, the valves 60 and 38 are closed, and the inflatable cuff 64 is deflated. A force applying system 34b is then activated by the control unit 24. While the force applying unit can be variously constructed, in the illustrated embodiment, the force applying system takes the form of an inflatable bladder, is illustrated in FIG. 5. The force applying system 34b can alternately be of a type that is mechanically or electrically activated, in which case the energy source 51 could take the form of a battery.

The generator 34b applies a force to the variable volume collection bag 86 to reduce its volume. The whole blood accumulated in the collection bag 86 is thus expressed or forced, through a conduit 84a into the plasma separator 90. The separator 90 will separate out 40-70% of the plasma in the whole blood passed through.

The whole blood passes through the separator 90 due to the force generator 34b in the direction 102. The plasma accumulates at the output port 90b and travels via the flexible tubing or conduit 92 to the plasma collection container 94. An arrow 104 indicates the direction of flow of the plasma.

The concentrated red blood cells, or residual blood component, exit from the separator 90 via the conduit 85, enter the conduit 78 and pass through the bubble trap and screen filter 80. The control unit 24 continuously monitors the electrical signal line 26a. In the event a bubble is detected in the trap 80, the clamp 36 is deenergized. Clamp 36, due to its internal spring biasing, immediately closes and blocks further fluid flow in the line 78 toward the donor D. An alarm condition can be indicated on the panel 66 and the operator can take corrective action.

If no bubbles are detected, the concentrated red blood cells will be returned to the donor D via the line 78 and the same single-lumen cannula 70 used for whole blood collection. During the collection phase and the separation/return phase, the donor D is continuously coupled to the system 10 by means of the single-lumen cannula 70 and the bi-directional fluid-flow conduit 72, 78. The collection of plasma occurs simultaneously with the return of the red blood cells.

Due to the features of the invention, the whole blood passes through the separator 90 for separation, and the red blood cells are returned to the donor solely in response to the force applied to the bag 86 by the generator 34b, and without the application of any additional external force.

When the whole blood collection bag 86 has been emptied, a four to seven minute process, the plasma has been collected in the bag 94, and the remaining concentrated red blood cells have been returned to the donor D. The valves 38, 60, 62 can then be opened and the process repeated. The return rate of concentrated red blood cells is in a range of 40-80 ml/minute. Because the bag 86 is filled and drained from the bottom, all whole blood is expressed from the container. Depending on the rate of collection of plasma in the bag 94 the process may be repeated two or three times.

The relatively low cost of the interconnected set 14 is an advantage of the system 10. The interconnected plastic members can be used in the collection of plasma from a single donor and then thrown away. In addition, since the bag 86 containing the collected blood remains continuously connected to the donor D, there is no chance that a donor D will accidentally receive the blood of another donor. Further, because the system 10 is continuously coupled to the donor D, the possibility of contamination is minimized.

The container 86 can be prefilled with sterile saline. The saline can be flushed from the container and the system 10 prior to the initiation of the initial blood collection cycle. Flushing or priming with saline insures a gas free system.

Figure 6:
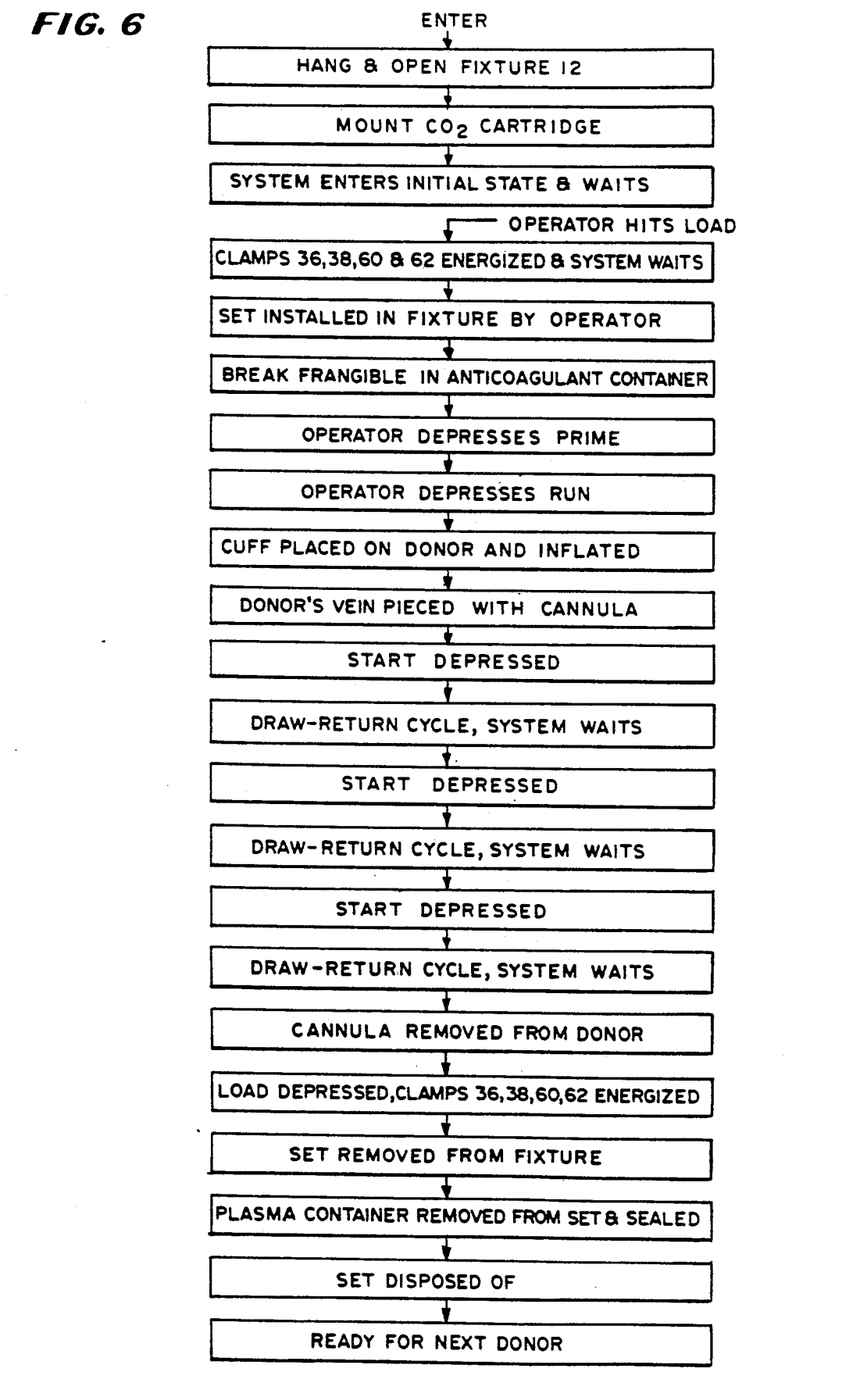
FIG. 6 is a flow diagram illustrating a method for plasmapheresis in accordance with the present invention.

An overall operational sequence is illustrated in the flow diagram of FIG. 6. The fixture 12 is hung on the donor bed the the cover 30 opened. A $CO_2$ cartridge C is removed from storage in the fixture 12 and inserted into the receptacle 52. This energizes the control unit and timer 24 which enters an initial state. When the operator is ready, the LOAD button 66a can be depressed. Upon sensing depression of the LOAD button 66a, the unit 24 energizes all clamps 36, 38, 60 and 64. The operator then installs the set 14 in the fixture 12.

The operator can then open the anticoagulant container 98 permitting a fluid flow to fill the line 76. The operator then depresses the PRIME button 66b. Clamps 38, 60 and 62 automatically close. A manually operated clamp 93 is closed by the operator to prevent fluid flow through line 92. The unit 24 then energizes the bladder 34b, via the line 24f to force saline from the bag 86 through the line 84a, the separator 90 and the lines 85 and 78. After the separator 90 has been filled with saline, clamp 38 is energized to open the line 84 to the flow of saline. When the entire set 14 has been flushed (and bag 86 is empty), and saline has run out of the cannula 70, the operator depresses the RUN button 66c. The system 10 then deenergizes the bladder 34b and closes clamps 36 and 38.

The operator then places the cuff 64 on the arm of the donor D, and the cuff 64 is inflated by the control unit and timer 24. The operator then enters a vein in the arm of the donor D with the sterile cannula 70. This step places the set 14 in a bi-directional fluid flow communication with the donor. This communication is continuously maintained through the following draw and return cycles. The operator then depresses the START button 66d to initiate the first draw and return cycle.

The first draw-return cycle is then commenced and clamps 36, 38, 60 and 62 are automatically opened. The clamp 93 is also opened by the operator. Blood, mixed with anticoagulant, flows under the influence of gravity and the pressure cuff 64 into the container 86. The unit 24 can be set for a predetermined draw cycle; for example, seven minutes. When bag 86 contains the desired amount of whole blood (for example, 500 ml), the housing 34 will prevent additional inflow and no further blood will be drawn from the donor.

Part way through the seven minute draw cycle, clamp 62 is deenergized by the unit 24. The flow of anticoagulant is then decreased during the completion of the draw cycle.

At the end of the seven minute draw cycle, clamps 60 and 38 are deenergized by the unit 24 along with the cuff 64. The bladder 34b is energized by the unit 24. Whole blood is forced through the separator 90. Plasma is collected in the container 94 and simultaneously the concentrated red blood cells are returned to the donor D via the bi-directional fluid flow conduit 72, 78 and the single lumen cannula 70. When the system 10 has completed the return cycle, the clamp 36 is deenergized. The system 10 waits until the operator again presses the START button 66d. Once the START button 66d has been depressed, the unit 24 reinflates the cuff 64 and initiates the next draw cycle.

After the third draw-return cycle the container 94 will contain a desired volume, for example, 500 ml of plasma. Housing 50 limits the separated plasma to the desired volume. In the event the container 94 becomes filled with plasma prior to the end of the third draw cycle, the housing 50 will block further inflow of plasma. The remainder of the whole blood will then be returned to the donor D. The cannula 70 is removed from the arm of the donor D. The operator again depresses the LOAD button 66a. All of the clamps are then energized by the unit 24. The set 14 can then be removed. The plasma container 94 can be removed from the set 14 and sealed as is conventional. The remainder of the set can then be thrown away. The system 10 is then ready for the next donor.

As before stated, the force application system 34b can take the form of a variety of devices to produce the necessary expressing forces. For example, a standard spring actuated plasma expressor of a type marketed by the Fenwal Division of Travenol Laboratories, Inc., Model No. 4R4414, could be used to apply force to the collection bag 86 thereby forcing the whole blood through the separator 90. It has been found, however, that such a device exerts a force which expresses the whole blood from the container 86 with an output pressure that varies substantially with time as the container 86 is being emptied.

Preferably the separator 90 will be a hollow membrane fiber filter. It would be desirable from the point of view of optimizing the design of the filter 90 to be able to express the whole blood from the container 86 at a substantially constant, predetermined, pressure.

For purposes of the present disclosure, the phrase "substantially constant predetermined pressure" shall mean a selected, applied pressure that remains essentially constant during the time period during which the whole blood is being forced from the container 86. A pressure variation of 10 or 20% during the first 80 to 90% of the time during which the container 86 is being emptied would still come within the present definition of a substantially constant pressure system.

The system 10 is thus a constant pressure system as opposed to a constant volume system, in which a relatively constant volume of fluid is pumped through the system per unit of time. The system 10, as a constant pressure system, has the further advantage that if a line such as 84a, 85 or 78 becomes crimped or blocked during the return portion of a draw-return cycle, the pressure present therein will not increase as might be the case in a constant volume system.

Figure 7A:
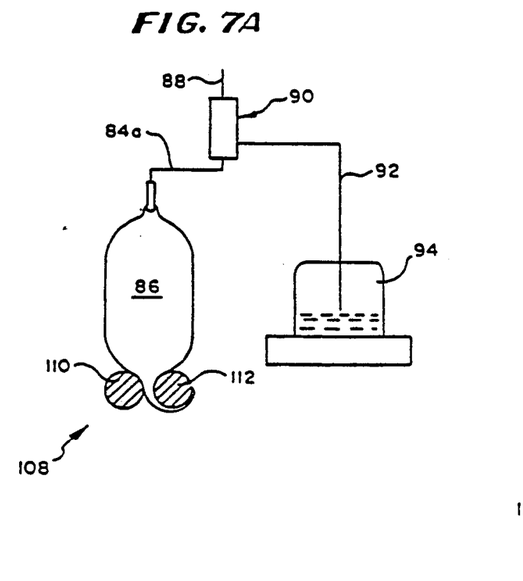
FIG. 7A is a side, schematic view of an apparatus for forcing whole blood out of the collection container.
Figure 7B:
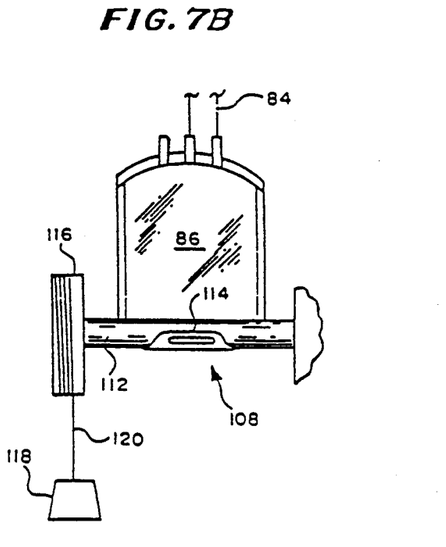
FIG. 7B is a front, schematic view of the apparatus of FIG. 7A.

A system 108 which will express the whole blood from the container 86 at a substantially constant predetermined pressure is illustrated in FIGS. 7A and 7B. This system 108, is formed with a pair of spaced apart rollers 110 and 112.

The rollers 110 and 112 are oriented so as to be parallel with a space there between. For example, the rollers might have a diameter on the order of ¾ of an inch and have an inter-roller gap of one-eighth of an inch. As illustrated in FIGS. 7A and 7B, a standard blood collection bag 86 is positioned with a lower tab located in a slot 114 in the roller 112.

In this embodiment, the self-contained energy source for the rollers 110, 112 includes means for releasably storing a quantity of energy to rotate the rollers 110, 112, as well as means for selectively introducing energy into the energy storage means.

While the above-described energy storage and introduction means can be variously constructed, as shown in FIG. 7B, they take the form of a pulley 116 attached to an end of the roller 112. A weight 118 is attached via a flexible cable or line 120 to the pulley 116. By recoiling the line 120 upon the pulley 116 after each use, the pulley 116 can be, in effect, "recharged" for subsequent use.

Experiments have indicated, that notwithstanding the fact that the blood container 86 is flexible and of irregular geometry, as the weight 118 unwinds due to the force of gravity, the force generating apparatus 108 will force the whole blood into the filter 90 at a substantially, constant pressure.

As the blood is forced from the bag 86, the empty portion of the bag 86 is wrapped around the roller 112. As the weight 118 continues to descend from the pulley 116, the bag 86 is continually drawn between the two rollers 110 and 112 and wrapped around the roller 112.

The system 108 will express the whole blood to the filter 90 at a substantially constant pressure on the order of 160 to 180 millimeters of mercury.

To generate pressures in a range of 160–180 mm of mercury, a weight 118 with a mass of 1950 g was used. The pulley 116 had a diameter of 15.9 cm. Larger or smaller pressures can be generated by varying the mass of the weight 118.

As the bag 86 empties, a spike of higher pressure appears after about 80% of the discharge or return period has passed. The effects of the spike can be attenuated by means of an elastic or stretchable, silicone tubing member attached to the weight 118 to slow its rate of descent during the last 20 percent of the discharge time. The presence of this spike does not preclude the roller system 108 from being a generator of substantially constant pressure as that phrase has been defined and used herein.

For example, a WACO 78170-10 elastic silicone tubing member was affixed to the weight 118. The time interval of substantially constant fluid pressure was, as a result, expanded from 80% to 90% of the discharge period. In this instance, a weight 118 with a mass of 4.81 kg was used in combination with a pulley 116 having a diameter of 5.71 cm.

Alternately, instead of using a weight such as the weight 118 as the energy source, a spring which exerts a constant force as it is being extended or as it is being retracted can be used to rotate the pulley 112. Such a spring, with a seven pound force has been used. It has been found experimentally that in connection with the system 108 the use of the constant force seven pound spring results in an output pressure on the order of 140 millimeters of mercury.

In this embodiment, the spring serves as the energy storage device which can be selectively recoiled, thereby "recharged", by the operator for subsequent use.

As an alternate to the roller system 108, and as earlier shown in the system 10 shown in FIG. 5, a commercially available inflatable bladder in a rigid container may be used. In this instance, the housing 34 of FIG. 1 corresponds to an external housing of the bladder 34b.

Figure 7C:
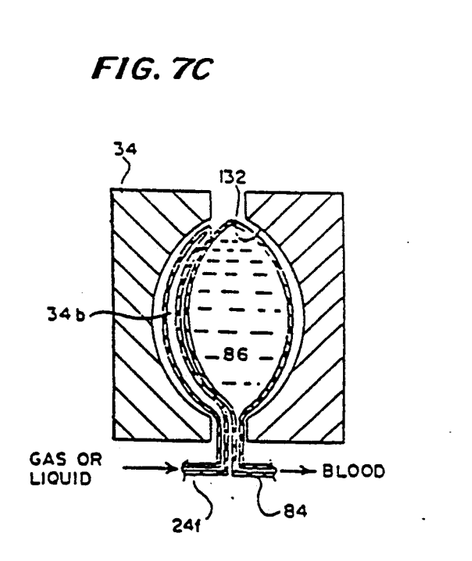
FIG. 7C is a side, schematic view of a preferred apparatus for forcing whole blood out of the collection container.

FIG. 7C illustrates a system utilizing such a force generating system. An external metal or rigid plastic housing 34 has a cavity 132 defined therein. The inflatable bladder 34b is positioned in the cavity 132. The blood collection bag 86 is placed in the cavity 132. Tubing 24f is provided to inflate the bladder 34b.

The bladder 34b is located adjacent the blood bag 86 and can be inflated by means of pressure from a gas or a liquid. For example, a regulated gas could be used, a liquid $CO_2$ cartridge could be used, or a gas or liquid under pressure due to a piston could also be used.

As the source of energy inflates the bladder 34b in the housing 34, the blood in the bag 86 is expressed into the tubing 84 at a substantially constant pressure. This pressure can be adjusted to be in a range of 160 to 180 millimeters of mercury as in the case with the dual roller system 108. The pressure should be adjusted in accordance with the resistance of the filter 90 and related flow circuits to provide physiologically acceptable return flow rates in a range of 40 to 80 cc per minute.

A further advantage of the bladder system is that the size of the cavity 132 and bladder 34b limit the volume of blood that can accumulate in the container 86. Hence, after the desired volume of blood has been accumulated in the container 86, the flow of whole blood essentially ceases. Similarly, housing 50 can be used to limit the volume of plasma that accumulates in the container 94.

In addition, unlike the system 108, the bladder system of FIG. 7C does not generate a spike of increased pressure and flow rate at the end of the return period. Instead, as the container 86 is emptied at the end of the return cycle, the generated pressure and flow rates decrease to zero.

Figure 8:
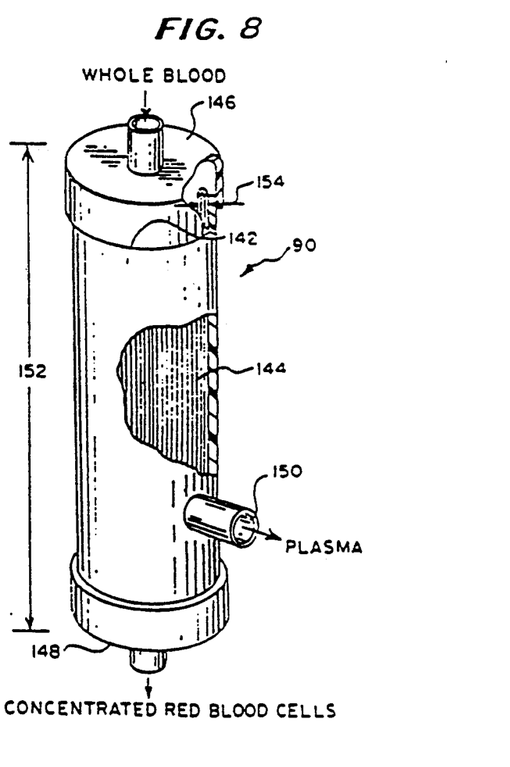
FIG. 8 is a fragmentary side view, partly in section, of a filter usable with the system of the present invention.

FIG. 8 illustrates an exemplary membrane filter usable with the system 10. The filter 90 includes a hollow cylindrical housing 142 in which is positioned a plurality of hollow fiber membranes 144. The housing 142 includes a blood inlet port 146, a blood outlet port 148 and a plasma output port 150. Fluid flow from the blood outlet port 148 is composed of concentrated red blood cells. This fluid can be regarded as a residual blood component.

The hollow fiber membranes, such as membranes 144, are suitable for contact with human blood and can be formed of polypropylene, polyethylene-co-vinyl alcohol, nylon, polysulfone or other materials. The fiber members 144 are oriented axially within the housing 142 such that the whole blood flows therethrough from end to end of the filter. The membranes are microporous and contain pores with diameters in a range of 0.1 to 5.0 microns preferably in a range of 0.2 to 0.6 microns.

One consideration in the design of filters such as the filter 90 is minimization of the risk of hemolysis. For given input pressures in a range of 160 to 180 millimeters of mercury, filter parameters of Table I define membrane filters with minimal risk of hemolysis for a given cost.

Each of the six filters defined by Table I includes hollow filtration fibers with each file having a length (L) 152 and an internal diameter (D) 154. The number of fibers (N) defines the number to be axially located in a give housing.

TABLE I

| P (mmHg) | N | L (cm) | D (m) |
|---|---|---|---|
| 100 | 3099 | 7.00 | 192 |
| 150 | 2209 | 7.00 | 189 |
| 100 | 2492 | 7.00 | 202 |
| 150 | 1731 | 7.00 | 198 |
| 100 | 1889 | 7.00 | 213 |
| 150 | 1347 | 7.00 | 209 |

Use of a filter with one set of the above parameters will result in extraction of 40 to 70% of the plasma in the whole blood which passes through the filter. Table I also illustrates in each instance the optimized parameters of a hollow membrane filter used in a system with a predetermined pressure drop (P) between the inlet port 146 and the outlet port 148 of each filter design. As can be seen, the number of fiber members decreases as the pressure drop across the filter is increased. Care must always be taken to insure that the force generating system provides enough pressure at the outlet port 148 to return the filtered blood to the donor D. Thus, for a predetermined pressure drop across the filter, it is possible to optimize the design of the filter. Operating the filter at the predetermined pressure drop optimizes collection of the separated blood component.

The present method and apparatus are particularly advantageous in that, given a substantially constant input pressure, the design and characteristics of the hollow fiber filter 90 can be optimized to provide efficient separation of the plasma component from the whole blood with minimal danger of hemolysis. In addition, the system 10 uses the disposable set 14 that is relatively inexpensive. The system 10 is easy to use and is portable to church basements or recreation halls where blood collection centers are often temporarily established.

The present method and apparatus have been disclosed in exemplary terms of separating and collecting plasma. The present invention, it will be understood, is not limited to plasma collection and separation. The separation and collection of a selected blood component, other than plasma, in accordance with the present apparatus and method are within the spirit and scope of the present invention. For example, leukocytes, lipids, lymphocytes, T-cell subsets, lipoprotein, other lipid moieties, auto-antibodies, immune complexes or the like could be separated and collected in accordance with the present method and apparatus.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. It is, of course, intended to cover by the appended claims all such modifications as fall within the scope of the claims.

What is claimed is:

1. A blood component collection method comprising the steps of:
   accumulating in a variable volume container a desired volume of whole blood from a donor,
   applying a force in excess of gravity upon the container to reduce its volume and thereby expressing the accumulated whole blood from the container through a conduit into a separator under continuous pressure which remains substantially constant despite variations in fluid resistance occurring in the conduit,
   separating the whole blood within the separator into component parts in response, at least in part, to the force applied during the force application step and without the application of any additional external pumping force, and
   collecting at least one of the component parts.

2. A method according to claim 1
   and further including the step of returning at least one of the component parts to the donor in response only to the force applied during the force application step.

3. A method according to claim 2
   wherein the steps of collecting at least one of the component parts and returning at least one of the component parts occur generally at the same time.

4. A method according to claim 2
   wherein, in the steps of accumulating whole blood from the donor and returning at least one of the component parts to the donor, only one single lumen vein access is used.

5. A method according to claim 1 and further including the step of introducing anticoagulant into the whole blood as it is being accumulated from the donor.

6. A method according to claim 1 wherein, during the separation step, a technique involving filtration is used.

7. A method according to claim 1 wherein whole blood is accumulated within the container and expressed from the container through the bottom of the container.

8. A method according of claim 1 wherein, during the separation step, the whole blood is separated into plasma and plasma-poor components, and wherein, during the collection step, the plasma is collected.

9. A method according to claim 8 and further including the step of returning the plasma-poor components to the donor in response only to the force applied during the force application step.

10. A method according to claim 9 wherein the step of collecting plasma and the step of returning plasma-poor components occur generally at the same time.

11. A method according to claim 9 wherein, in the steps of accumulating whole blood from the donor and returning the plasma-poor components to the donor, only one single lumen vein access is used.

12. A method according to claim 8 and further including the step of introducing anticoagulant into the whole blood as it is being accumulated from the donor.

13. A method according to claim 8 wherein, during the separation step, a technique involving filtration is used.

14. A method according to claim 1 or 8 wherein, in the step of accumulating the whole blood, the whole blood is accumulated in the variable volume container in response to the internal blood pressure of the donor and without an external pumping force.

15. A method according to claim 14 wherein, in the step of accumulating the whole blood, a pressure cuff is used to increase the internal blood pressure of the donor.

16. A blood component collection method comprising the steps of:
accumulating in a flexible plastic bag a desired volume of whole blood from a donor in response to the internal blood pressure of the donor and without an external pumping force.,
applying a force in excess of gravity upon the flexible plastic bag to reduce its volume and thereby expressing the accumulated whole blood from the container through a conduit into a separator under continuous pressure which remains substantially constant despite variations in fluid resistance occurring in the conduit,
separating the whole blood within the separator into component parts in response, at least in part, to the force applied during the force application step and without the application of any additional external pumping force, and
collecting at least one of the component parts.

17. A method according to claim 16 and further including the step of returning at least one of the component parts to the donor in response only to the force applied during the force application step.

18. A method according to claim 16 or 17 wherein, in the step of accumulating the whole blood, a pressure cuff is used to increase the internal blood pressure of the donor.

19. A plasmapheresis method comprising the steps of establishing a flow of whole blood from a donor,
collecting the whole blood in a variable volume container,
terminating the flow of whole blood into the container when a desired volume of whole blood has been collected therein,
applying an external force upon the container in excess of gravity to reduce the volume of the container and establish a flow of whole blood from the container and through a conduit into a membrane filtration device under continuous pressure which remains substantially constant despite variations in fluid resistance occurring in the conduit to separate the whole blood into plasma and plasma-poor components,
collecting the plasma, and
returning all the plasma-poor components from the membrane filtration device directly to the donor in a path that bypasses the membrane filtration device.

20. A method in accordance with claim 19 wherein, in the steps of establishing the flow of whole blood from the donor and returning the second blood components to the donor, the same single lumen phlebotomy needle is used.

21. A method in accordance with claim 19 or 20 wherein the steps of collecting the plasma and returning the plasma-poor components occur generally at the same time.

22. A method in accordance with claim 19 wherein the membrane filtration device includes a plurality of hollow fibers.

23. A plasmapheresis method according to claim 19 wherein the flow of whole blood from the variable volume container through the membrane filtration device proceeds in response only to the application of force upon the variable volume container.

24. A method in accordance with claim 23 and wherein the step of returning the plasma-poor components proceeds in response only to the force applied during the force application step.

25. A method according to claim 19 wherein, in the step of establishing the flow of whole blood, the whole blood flows into the variable volume container in response to the internal blood pressure of the donor and without an external pumping force.

26. A method according to claim 25 wherein, in the step of establishing the flow of whole blood, a pressure cuff is used to increase the internal blood pressure of the donor.

27. A blood component collection system comprising:
means for accumulating in a variable volume container a desired volume of whole blood from a donor,
means for separating whole blood into component parts, conduit means for conveying whole blood from the variable volume container to the separation means, and means for applying a force in excess of gravity upon the container to reduce its volume and for expressing the accumulated whole blood from the container through the conduit means into the separation means under continuous pressure which remains substantially constant despite variations in fluid resistance occurring in the conduit means for separating the whole blood into component parts in response, at least in part, to the force applied upon the container and without the application of any additional external pumping force.

28. A method according to claim 27 and further including means for returning at least one of the component parts to the donor in response only to the force applied during the force application step.

29. A blood component collection system according to claim 28 wherein the whole blood accumulation means and the component return means include the same single lumen phlebotomy needle.

30. A blood component collection system according to claim 27 and further including means for introducing anticoagulant into the whole blood as it is being accumulated in the variable volume container.

31. A blood component collection system according to claim 27 wherein the separation means includes a filter.

32. A blood component collection system according to claim 27 wherein the force application means includes an inflatable bladder adjacent to the container for applying force thereto.

33. A blood component collection system according to claim 27 wherein the variable volume container comprises a flexible plastic bag.

34. A blood component separation system comprising
a variable volume container for accumulating a volume of blood,
a separation device in flow communication with the container for separating the accumulated blood into components,
a module containing a releasable charge of energy, and
a fixture comprising
a housing for releasably retaining the container and the separation device,
first means for releasably receiving the module, and
second means operatively connected to the first means for releasing the charge of energy and for applying, in response to the released charge of energy, a force in excess of gravity upon the container to reduce its volume and express the accumulated blood into the separation device to undergo separation in response to the applied force and without the application of any additional pumping force.

35. A blood component collection system according to claim 34 wherein the force application means comprises and inflatable bladder, and
wherein the module comprises a cartridge of fluidic energy for inflating the bladder.

36. A blood component separation system comprising
a variable volume container for accumulating a volume of blood,
a separation device in flow communication with the container for separating the accumulated blood into components, and
a fixture comprising
a housing for releasably retaining the container and the separation device, means on the housing for releasably storing a quantity of energy,
means for selectively introducing energy into the energy storage means, and means operatively connected with the energy storage means for releasing the quantity of stored energy and for applying, in response to the released quantity of stored energy, a force in excess of gravity upon the container to reduce its volume and express the accumulated blood into the separation device to undergo separation in response to the applied force and without the application of any additional pumping force.

37. A system according to claim 36 wherein the force application means comprises an inflatable bladder, and
wherein the energy storage means is operative for releasably storing fluid energy for inflating the bladder.

38. A self-contained component separation fixture comprising
means for releasably retaining a variable volume container in flow communication with a separation device operative for separating the fluid contents of the variable volume container into one or more component parts,
means for applying a force in excess of gravity upon the container to reduce its volume and express the contents into the separation device to undergo separation in response to the applied force and without the application of any additional pumping force, and
means for releasably receiving a module containing a releasable charge of energy and for selectively releasing the energy charge to operate the force application means.

39. A fixture according to claim 38 wherein the force application means comprises and inflatable bladder, and
wherein the module comprises a cartridge of fluidic energy for inflating the bladder.

40. A self-contained component separation fixture comprising
means for releasably retaining a variable volume container in flow communication with a separation device operative for separating the fluid contents of the container into one or more component parts,
means for releasably storing a quantity of energy,
means for selectively introducing energy into the energy storage means, and
means operatively connected with the energy storage means for releasing the quantity of stored energy and for applying, in response to the released quantity of stored energy, a force in excess of gravity upon the container to reduce its volume and express the contents into the separation device to undergo separation in response to the applied force and without the application of any additional pumping force.

41. A fixture according to claim 39 wherein the force application means comprises an inflatable bladder, and wherein the energy storage means is operative for releasably storing fluid energy for inflating the bladder.

42. Apparatus according to claim 34 or 36 or 38 or 40 wherein the force application means establishes a continuous pressure which remains substantially constant while separation occurs within the separation device.

43. Apparatus according to claim 34 or 36 or 38 or 40 wherein the separation device comprises a membrane separation device.

44. Apparatus according to claim 43 wherein the force generating means establishes a continuous pressure which remains substantially constant while separation occurs within the separation device.

45. Apparatus according to claim 44 wherein the variable volume container comprises a flexible bag.

46. Apparatus according to claim 43 wherein the variable volume container comprises a flexible bag.

* * * * *